United States Patent
Nagashima et al.

(10) Patent No.: US 6,755,075 B2
(45) Date of Patent: Jun. 29, 2004

(54) ULTRA MICRO INDENTATION TESTING APPARATUS

(75) Inventors: Nobuo Nagashima, Ibaraki (JP); Kensuke Miyahara, Ibaraki (JP); Saburo Matsuoka, Ibaraki (JP)

(73) Assignees: Japanese Science and Technology Corporation, Saitama (JP); National Institute for Materials Science, Ibaraki (JP)

( * ) Notice: Subject to any disclaimer, the term of this patent is extended or adjusted under 35 U.S.C. 154(b) by 142 days.

(21) Appl. No.: 09/958,477

(22) PCT Filed: Feb. 9, 2001

(86) PCT No.: PCT/JP01/00927

§ 371 (c)(1),
(2), (4) Date: Nov. 21, 2001

(87) PCT Pub. No.: WO01/59426

PCT Pub. Date: Aug. 16, 2001

(65) Prior Publication Data

US 2003/0070475 A1 Apr. 17, 2003

(30) Foreign Application Priority Data

Feb. 10, 2000 (JP) ........................................ 2000-034225

(51) Int. Cl.[7] ................................................ G01N 3/48
(52) U.S. Cl. ............................................ 73/105; 73/81
(58) Field of Search ................................ 73/105, 12.09, 73/81, 82

(56) References Cited

U.S. PATENT DOCUMENTS 5,319,960 A * 6/1994 Gamble et al. ............... 73/105
6,396,054 B1 * 5/2002 Kley

FOREIGN PATENT DOCUMENTS

JP 8-159941 6/1996
JP 10-185802 7/1998

OTHER PUBLICATIONS

IBM Corporation Technical Disclosure Bulletin, Armonk, NY, pp. 194–195, vol. 34, No. 10A, Mar. 1992.*
"Researches On Nanoscopic Material Damage Evaluation", Research Report 20, National Research Institute for Metals, pp. 1–50 total, (including pp. 1–33, Figs. 1–20 and Tables 1 and 2), No Date.

* cited by examiner

Primary Examiner—Robert Raevis
(74) Attorney, Agent, or Firm—Wenderoth, Lind & Ponack L.L.P.

(57) ABSTRACT

An ultra micro indentation testing apparatus comprises: a lever stand provided with a center lever having a silicon probe and a diamond indenter disposed therein; a moving mechanism for moving the lever stand in a triaxial direction; in indentation mechanism for pushing the diamond indenter in a sample; a displacement gage for measuring a displacement of the silicon probe or the diamond indenter; and an optical picture device for positioning the silicon probe or the diamond indenter and observing the surface of the sample. The apparatus has, in combination, a hardness measuring function based on the measurement of the force and depth of the diamond indenter pushed in the surface of the sample, an atomic force microscopic function of acquiring the shape of the surface of the sample based on a displacement of the diamond indenter or the silicon probe, and an optical microscopic function of observing the surface of the sample by the optical picture device. Furthermore, the testing apparatus is equipped with both the function of measuring the hardness of the surface of material in a ultra micro region and the surface observing function with high accuracy.

29 Claims, 23 Drawing Sheets

FRONT VIEW            SIDE VIEW 1  2  3

(a)

(b)

ULTRA MICRO INDENTATION TESTING APPARATUS

TECHNICAL FIELD

The present invention relates to an ultra micro indentation testing apparatus. More particularly, the present invention relates to a novel ultra micro indentation testing apparatus, which can achieve minute hardness measurement or material surface observation for evaluating mechanical characteristics of the fine structure of a functional material, and which is useful for evaluating the functional material or setting guidelines for development of the functional material.

BACKGROUND ART

In the electric, electronic or communication industry, high performance and material advancement have been remarkably developed in recent years. An important problem to be solved is to measure the hardness or Young's modulus of a surface on a crystalline grain boundary, or of a minute region in the vicinity of the tip of a crack, a thin film, an oxide film at the surface of the material, a laminated film or an ion implantation layer with high accuracy at a nanoscopic level as one of techniques for supporting the high performance and advance of the material.

A Vickers hardness tester has been conventionally used for the purpose of measuring the surface hardness of material. Moreover, there has been recently proposed a surface hardness measuring method, in which an atomic force microscope (AFM) is used as it is. However, it is difficult to achieve the accuracy at a nanoscopic level in the measurement by the above-described conventional methods.

The inventors of the present application have proposed a novel surface hardness measuring apparatus capable of highly accurate measurement at a nanoscopic level in place of the above-described conventional measuring methods (Japanese Patent No. 2725741). As shown in FIG. 22, the apparatus is a surface hardness measuring apparatus comprising a center lever (201) having a probe (202) disposed at the center thereof, a center lever stand (204) for fixing the center lever (201), a uniaxial actuator (205) for the center lever, a triaxial observing actuator (207) for changing the position of a sample, and a displacement gage (206). The probe (202) disposed in the center lever (201) is vertically pushed in the surface of a sample (203), and then minute hardness is measured by measuring a force and a penetration depth at that time. Furthermore, a tension adjusting means for adjusting an interval between lever arms (214) and (215) opposite to each other in the center lever stand (204) so as to adjust tension to be applied to a center lever is interposed between the lever arms (214) and (215) in one example of modes, as shown in FIG. 23. The tension adjusting means includes a screw means (213) which abuts against the inside of one of the lever arms at one end thereof, and spring members (216) and (217) respectively consisting of the lever arms opposite to each other in the center lever stand by forming cutouts.

The above-described invention by the inventors of this application has enabled the hardness of material to be measured at a nanoscopic level in an indentation test. However, since an indenter for carrying out the indentation test also serves as a probe for observing a surface, there has arisen a problem of an insufficient resolution at the time of the observation. In order to solve such a problem, the hardness measurement and the surface observation might be individually performed by two different testing machines. However, such means for solving the problem is not desired from the viewpoints of the difficulty of reproducing the same position of a sample in the two different testing machines, efficiency of tests or cost reduction of the testing machines.

SUMMARY OF THE INVENTION

The present invention has been accomplished in view of the above-described circumstances. Therefore, the problem to be solved by the present invention is to provide a testing apparatus equipped with both the function of measuring the hardness of the surface of material in an ultra micro region and the function of observing the surface by an AFM with high accuracy.

According to the present invention, in order to solve the above-described problem, an ultra micro indentation testing apparatus includes a lever stand provided with a center lever having a probe and an indenter disposed therein; a moving mechanism for moving the lever stand in a triaxial direction; an indentation mechanism for pushing the indenter in a sample; a displacement gage for measuring a displacement of the probe or the indenter; and an optical picture device for use in (assisting with) positioning the probe or the indenter and observing the surface of the sample. The apparatus has, in combination, a hardness measuring function based on measurement of the force and depth of the indenter pushed in the surface of the sample, an atomic force microscopic function of acquiring the shape of the surface of the sample based on a displacement of the probe or the indenter, and an optical microscopic function of observing the surface of the sample by the optical picture device.

Furthermore, according to the present invention, a hole for setting a center lever is formed at the center of the lever stand; a groove for setting the center lever is formed at the side face of the lever stand; the indenter is provided at part of the center lever; and a positioning mark is made at part of the center lever.

Moreover, according to the present invention, a plurality of probes are provided in the lever stand; a plurality of center levers are provided in the lever stand; the probe is made of silicon or a substance like silicon, which is easily machined into a sharp shape, and the indenter is made of diamond or a hard substance like diamond; and the above-described apparatus may further comprise a mechanism for remotely controlling the movement of the lever stand with the accuracy on the order of a micrometer.

DETAILED DESCRIPTION OF THE INVENTION

Modes for carrying out the present invention will be explained below.

An ultra micro indentation testing apparatus according to the present invention is equipped with a function of hardness measurement, a function of an atomic force microscope and the function of an optical microscope, and further, the testing apparatus is provided inside thereof with mechanisms for respectively achieving the functions.

Figure 1:
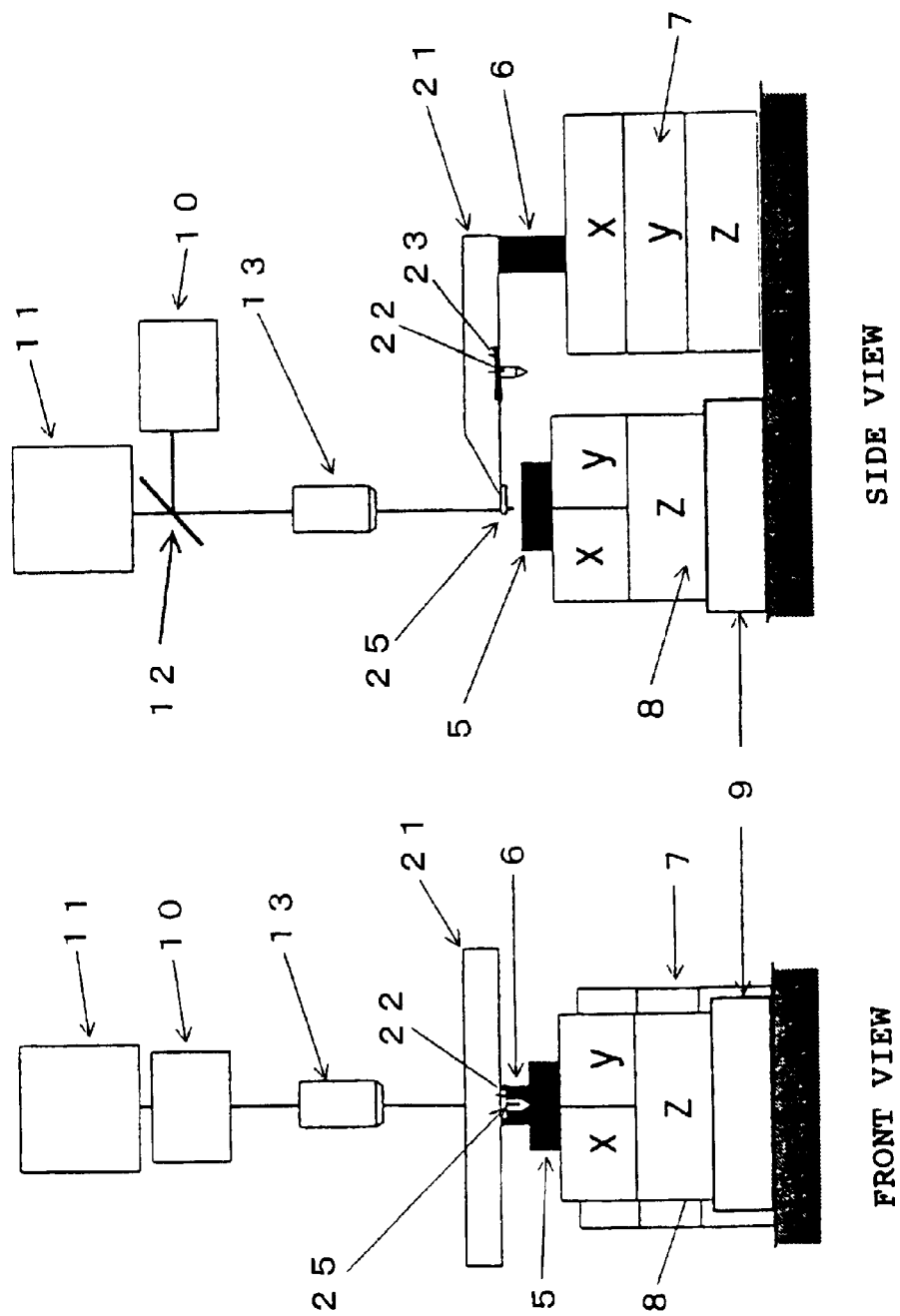
FIG. 1 is a view schematically showing the configuration of a super micro indentation testing apparatus according to the present invention.

For example, as shown in FIG. 1, the ultra micro indentation testing apparatus according to the present invention comprises: a lever stand (21) including a center lever (23) with a silicon probe (25) and a diamond indenter (22) fixed thereto; an actuator (6) for controlling a load when the diamond indenter (22) is pushed into a sample (5); a triaxial wide-area servo motor (7) for moving the lever stand; a triaxial precision actuator (8) and a uniaxial wide-area servo motor (9) for moving the sample at the time of measurement; and a vertical displacement gage (10) for measuring a displacement of the silicon probe (25) or the diamond indenter (22) at the time of measurement by an atomic force microscope.

Just above the sample is provided an optical picture device (11) such as a CCD camera, which is used to observe a surface at the time of measurement using an optical microscope and to position the silicon probe (25) on the diamond indenter (22) at the time of measurement by the atomic force microscope. There is provided a half mirror (12) for refracting a laser beam which is emitted from or incident into the vertical displacement gage (10). The vertical displacement gage (10) is located out of a visual field of the optical picture device (11) in such a manner as not to prevent photographing by the optical picture device (11). Furthermore, an objective lens (13) is interposed between the optical picture device (11) and the vertical displacement gage (10), and the sample (5). The triaxial wide-area servo motor (7) serving as a mechanism for moving the lever stand is provided with a mechanism for remotely controlling the lever stand with accuracy in the order of micrometer.

Figure 2:
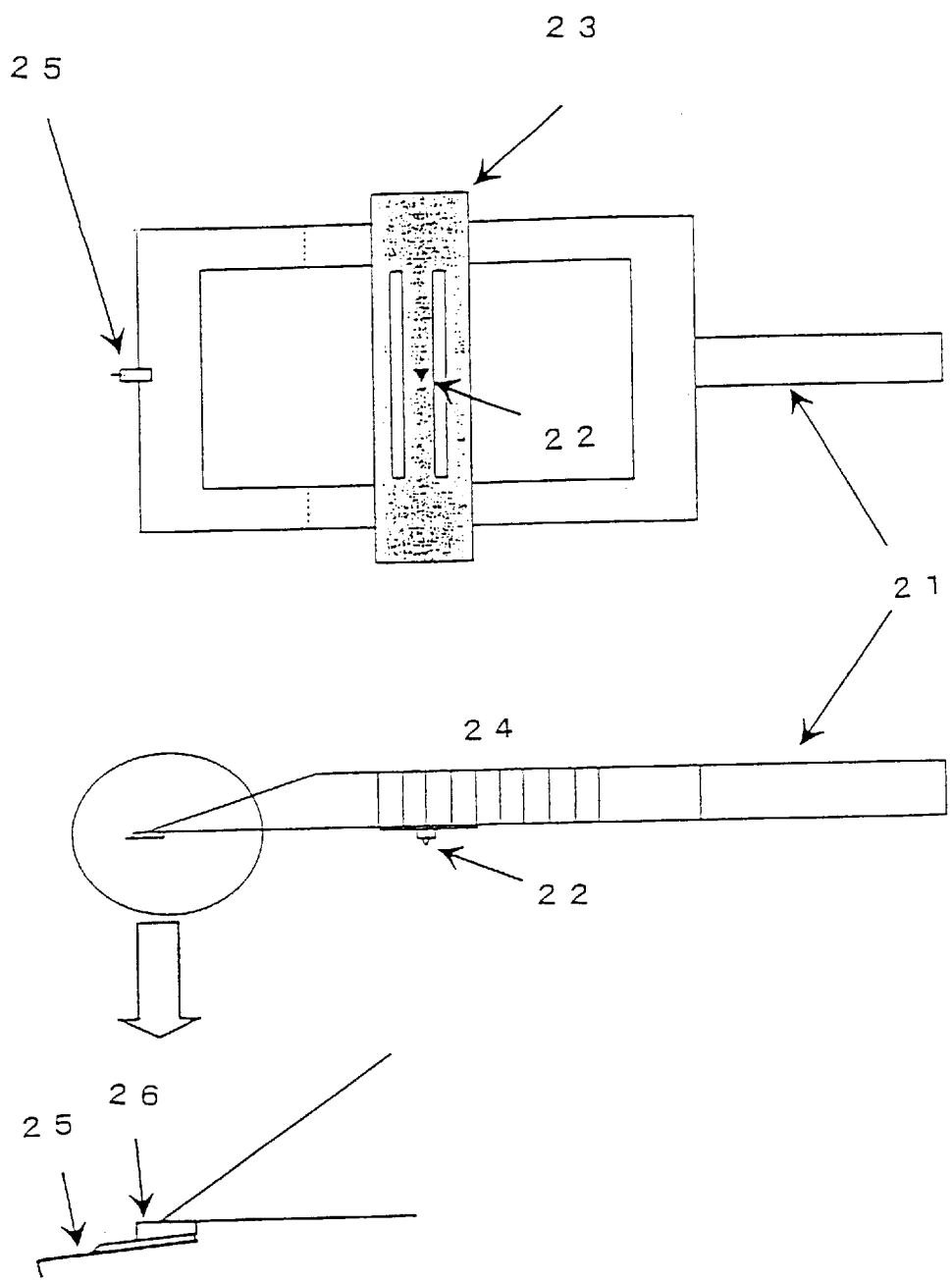
FIG. 2 is a view schematically showing the configuration of a lever stand in the super micro indentation testing apparatus according to the present invention.

The lever stand (21) is connected to the actuator (6), and can be moved in a vertical direction. As shown in FIG. 2, the lever stand (21) is formed into a U shape. To an opened portion of the lever stand is attached the center lever (23) provided with the diamond indenter (22). At the side face of the lever stand (21) are formed grooves (24) as guide lines for use in attaching the center lever (23). Moreover, the upper surface (i.e., a side facing the optical picture device) of the center lever (23) is marked for positioning. In the case where an indentation test by the diamond indenter and atomic force microscopic measurement by the silicon probe are repeated at a constant position a plurality of times, the positioning is performed based on the mark shot by the optical picture device.

Additionally, the silicon probe (25) is attached to the tip of the lever stand (21). More particularly, an adapter (26) such as a vibration type actuator with a silicon probe connecting mechanism is attached to the tip of the adapter (26). The adapter (26) is inclined, so that the tip of the silicon probe (25) is inclined downward accordingly.

Needless to say, the present invention does not restrict the probe to the silicon probe (25), and does not restrict the indenter to the diamond indenter (22). For example, various kinds of hard substance like diamond may be used. Incidentally, in current circumstances, silicon and diamond are suitable from the viewpoints of safeness, measurement accuracy and the like.

Figure 3:
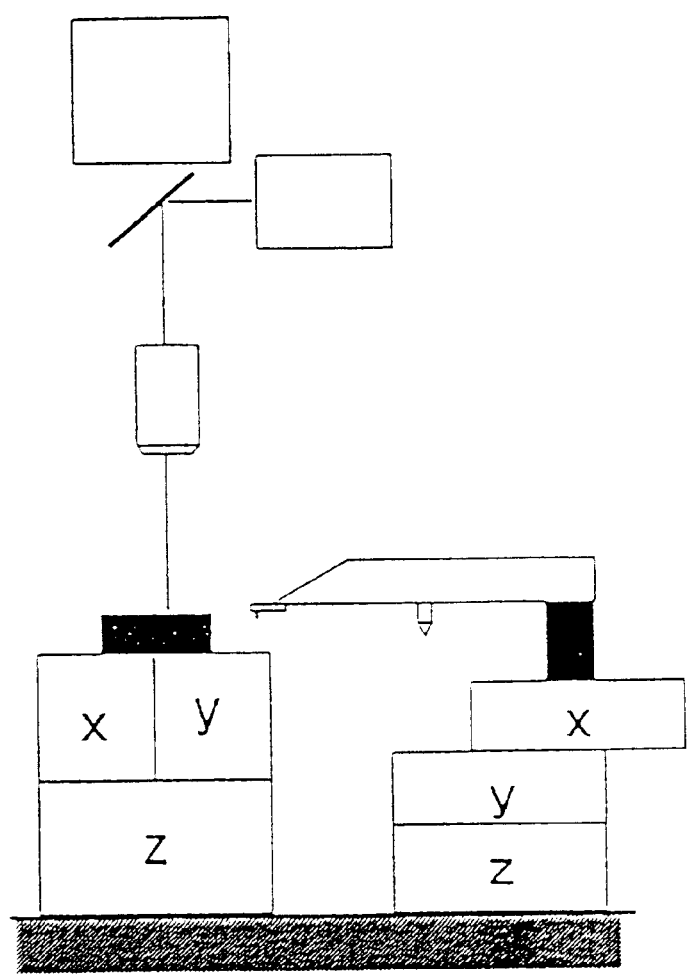
FIG. 3 is a view schematically showing a mode of an optical microscopic function in the super micro indentation testing apparatus according to the present invention.
Figure 4:
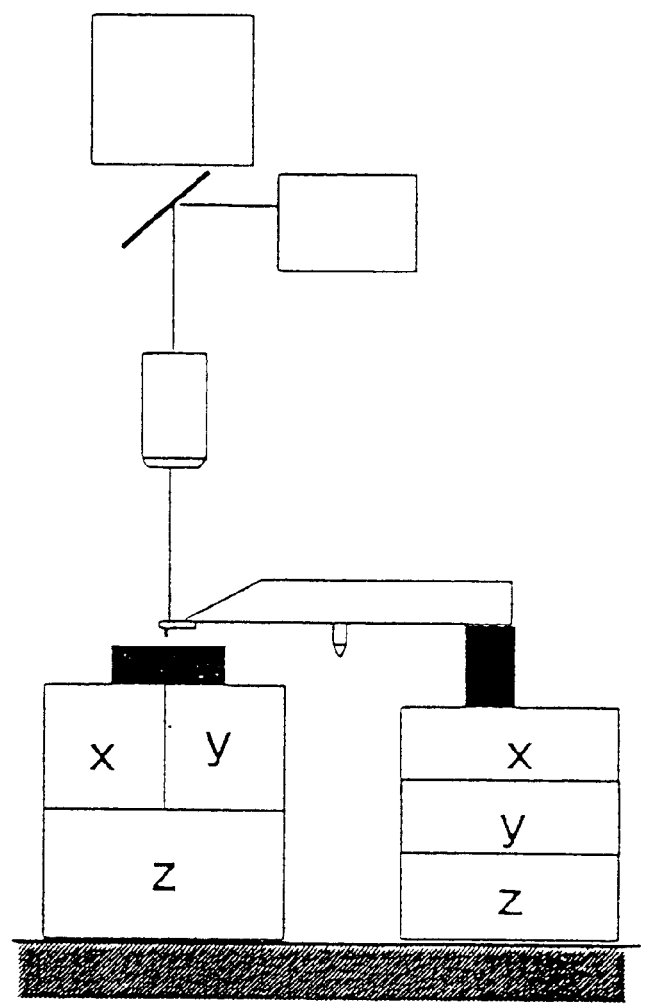
FIG. 4 is a view schematically showing a mode of an atomic force microscopic function in the super micro indentation testing apparatus according to the present invention.
Figure 5:
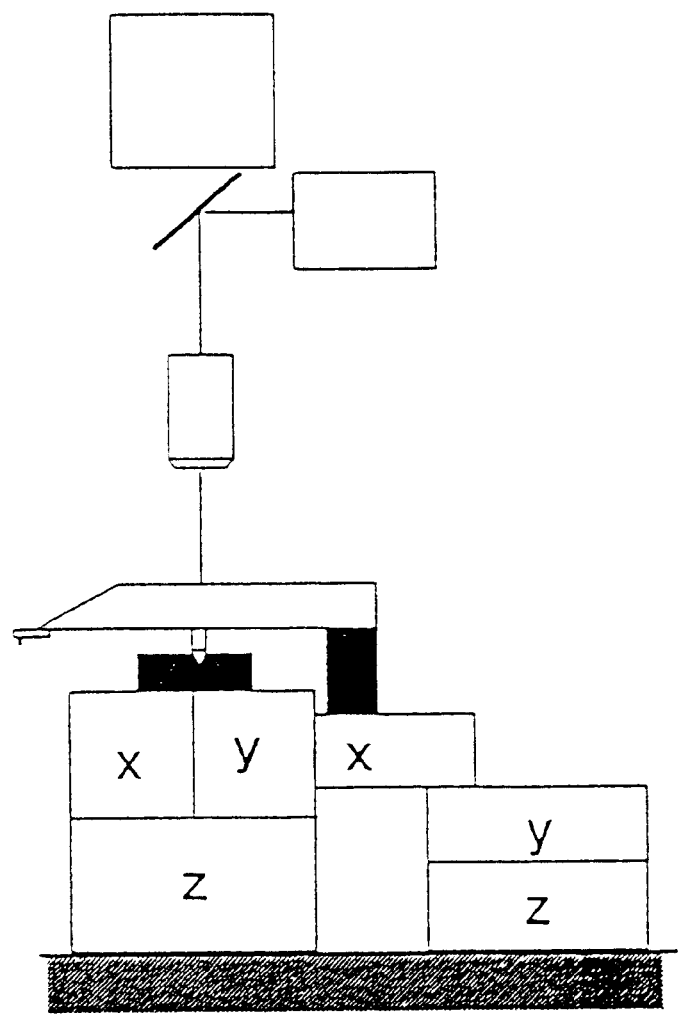
FIG. 5 is a view schematically showing a mode of a hardness measuring function in the super micro indentation testing apparatus according to the present invention.

Next, an explanation of modes of three functions (i.e., a mode of an optical microscopic function, a mode of a hardness measuring function, and a mode of an atomic force microscopic function) equipped in the ultra micro indentation testing apparatus according to the present invention will be provided with reference to FIGS. 3 to 5.

First, in the optical microscopic function mode, as shown in FIG. 3, the lever stand provided with the diamond indenter and the silicon probe is fixed out of the visual field of the optical picture device. Then, the sample is moved by the triaxial precision actuator and the uniaxial wide-area servo motor.

In the atomic force microscopic function mode, as shown in FIG. 4, the tip of the silicon probe is fixed at the center of an image to be shot by the optical picture device, (i.e., at a vertical displacement measuring point) by the triaxial wide-area servo motor. Then, the sample is scanned in the direction of a horizontal plane by the triaxial precision actuator, so that the sample is measured by the atomic force microscope. In this mode of the atomic force microscopic function, the diamond indenter may be used in place of the silicon probe, so as to observe the shape of the surface of the sample. The resolution of a resultant observed image when the diamond indenter is used is somewhat lower than the resolution when the silicon probe is used.

In the hardness measuring function mode, as shown in FIG. 5, the portion just above the diamond indenter is fixed at the center of the image to be shot by the optical picture device (i.e., at the vertical displacement measuring point) by the triaxial wide-area servo motor, and the diamond indenter is then pushed into the sample by the uniaxial actuator. The hardness of the surface of the sample is measured by measuring an indentation load and a penetration depth at that time.

These modes of the three functions are implemented in combination, thus achieving the measurement of the surface of the sample by the optical microscope, the hardness measuring test by indentation and the measurement of the indentation by the atomic force microscope without moving the sample.

The triaxial wide-area servo motor serving as the mechanism for moving the lever stand is provided with a mechanism for remotely controlling the lever stand with accuracy in the order of a micrometer. Therefore, the position of the lever stand in each of the function modes can be determined with accuracy in the order of a micrometer.

Figure 6:
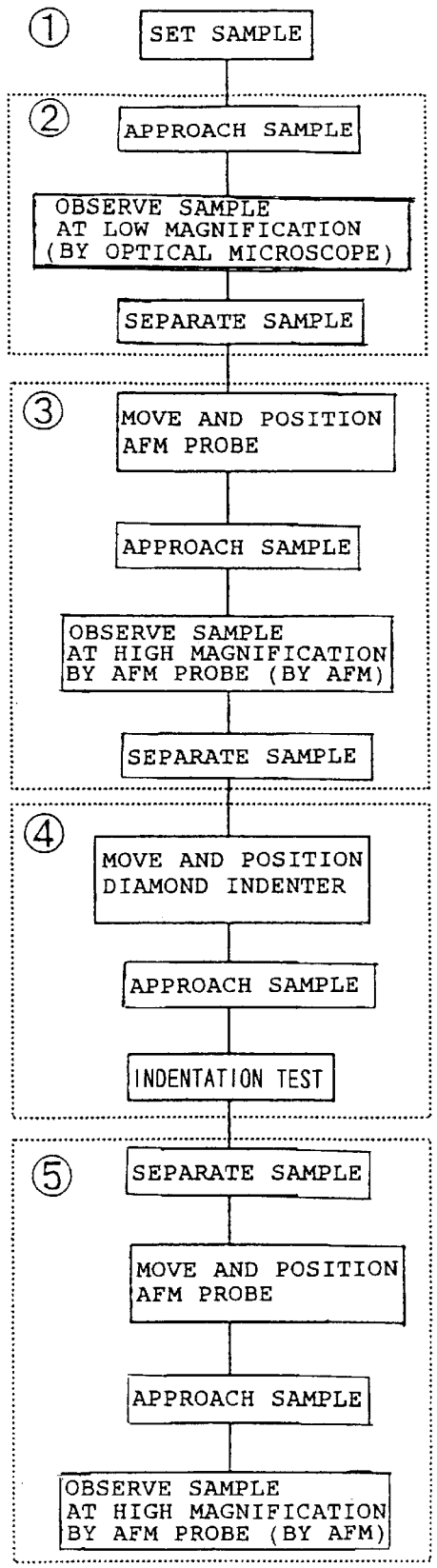
FIG. 6 is a flowchart illustrating one example of measuring procedures by using the super micro indentation testing apparatus according to the present invention.
Figure 7:
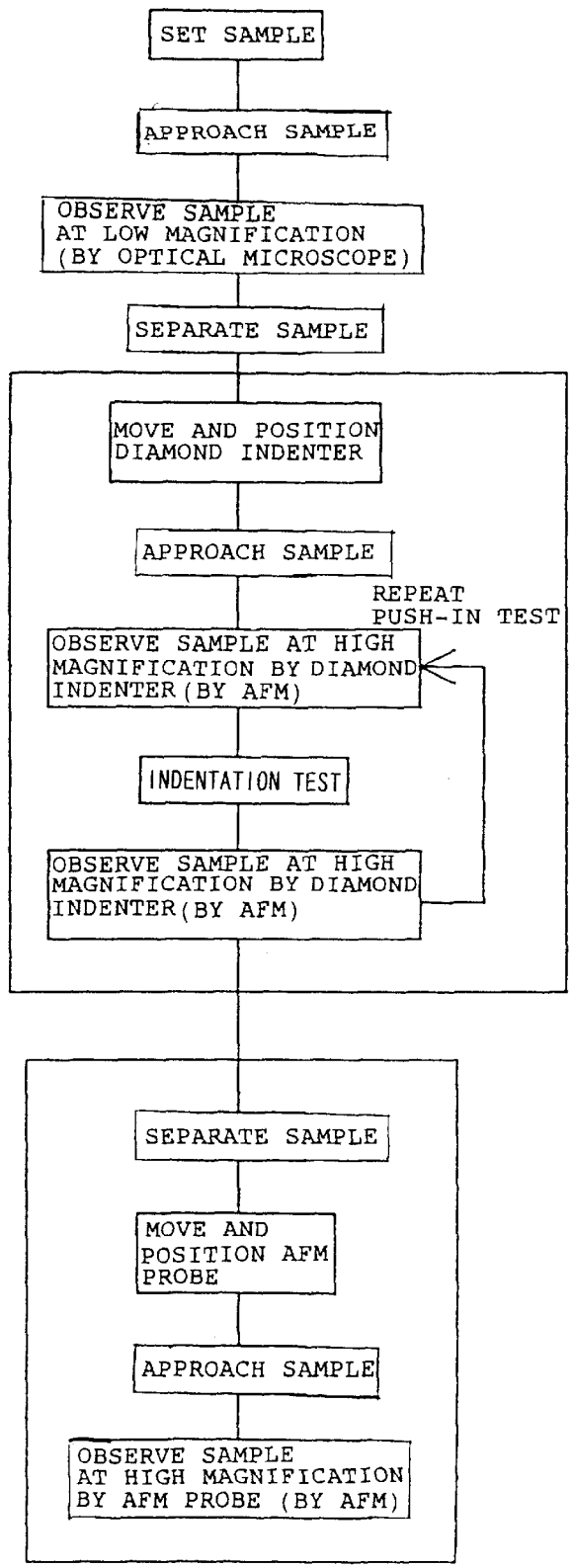
FIG. 7 is a flowchart illustrating another example of the measuring procedures by using the super micro indentation testing apparatus according to the present invention.

A specific measuring procedure is exemplified in, for example, a flowchart of FIG. 6. That is, the sample is set (1); and the surface of the sample is observed and the vertical displacement measuring point is positioned in the optical microscopic function mode (2). Subsequently, the sample is observed by the atomic force microscope having a high resolution in the atomic force microscopic function mode by the use of the silicon probe (an AFM probe) before the indentation hardness measuring test (3); and the indentation hardness measurement is performed by the use of the diamond indenter in the hardness measuring function mode (4). Further, the indentation is observed by the atomic force microscope having a high resolution in the atomic force microscopic function mode (5). Alternatively, in accordance with the procedure illustrated in FIG. 7, the test may be made on a piece of sample a plurality of times, thereby measuring the hardness distribution of the surface of the sample.

It is understood that the measuring procedure using the ultra micro indentation testing apparatus according to the present invention should not be restricted to the above-illustrated procedures. Therefore, the process can adopt optimum procedures according to specific conditions.

Figure 8:
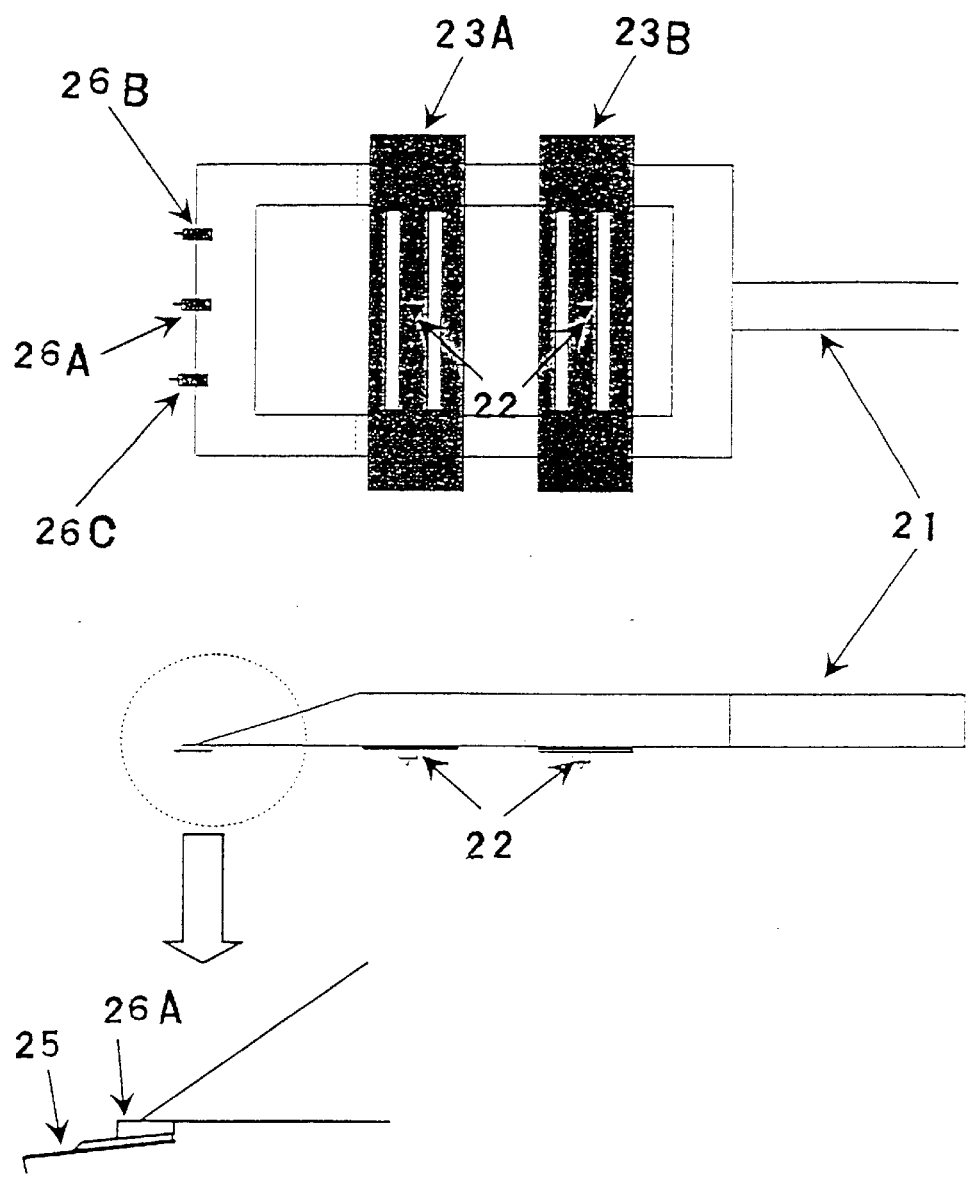
FIG. 8 is a view schematically showing the configuration of one example of the lever stand provided with a plurality of probes and indenters.

Furthermore, according to the present invention, there may be provided a lever stand having a plurality of levers with indenters for performing an indentation test and a plurality of levers for AFM observation, as shown in FIG. 8. In this case, an indenter or a probe for use in performing the indentation test or the AFM observation can be freely selected as necessary.

Figure 9:
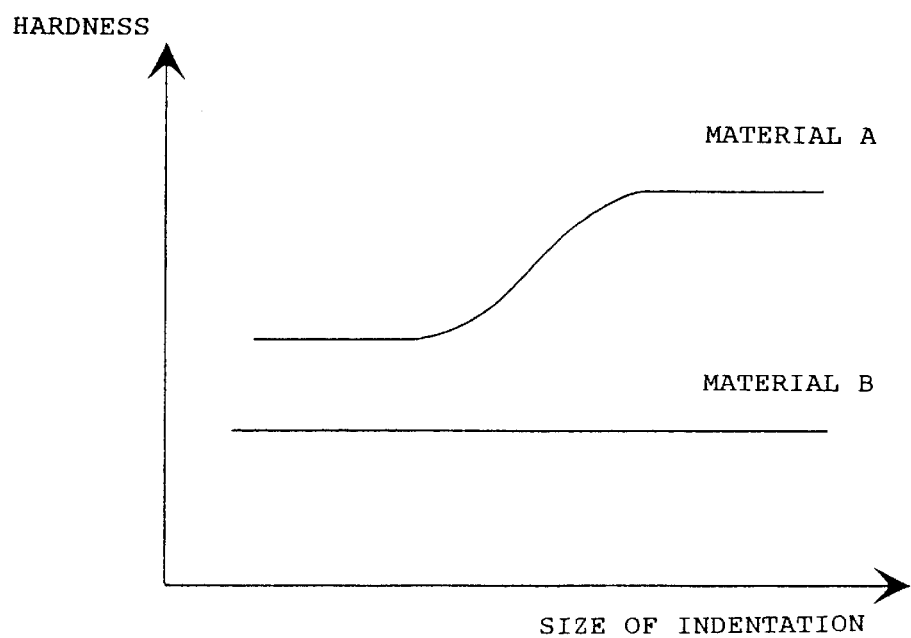
FIG. 9 is a graph schematically illustrating the relationship between the size and depth of an indentation.

FIG. 9 is a graph illustrating one example of a reason for requiring a plurality of levers each having an indenter for an indentation test. The abscissa indicates the size of an indentation, and the ordinate indicates the measured hardness. With respect to a material A, the smaller the size of the indentation, the lower the hardness. In contrast, with respect to a material B, the hardness is constant irrespective of the size of the indentation. This is important information verifying that strengthening mechanisms of the two materials are different. In the case where the dependency of the hardness on the indentation is acquired, the test is made on the indentation force within a wide range, so that it is necessary to use a plurality of levers each having an indenter for the indentation test according to a high load or a low load.

Also with respect to the lever for the AFM observation, it may be necessary to attach a plurality of levers to the lever stand, such as a special measuring lever for vertically vibrating a probe or a spare lever since the AFM probe is liable to be scratched, in addition to normal AFM observation.

FIG. 8 illustrates one example, in which three AFM observing levers are constituted by attaching a silicon probe (25) to each of a normal adapter (26A), a vibrating adapter (26B) and a spare adapter (26C). Furthermore, two center levers respectively provided with diamond indenters (22) are constituted of a center lever (23A) for a low load and a center lever (23B) for a high load.

The present invention is as described above. Further, a specific description will be given below by way of preferred embodiments.

PREFERRED EMBODIMENTS

The apparatus having any one of the configurations shown in FIGS. 1 to 7 can be used as the ultra micro indentation testing apparatus according to the present invention, thus implementing the hardness measurement and the atomic force microscopic measurement of an electrolytic polishing surface of each of tungsten single crystal and SCM 440 steel.

Figure 10:
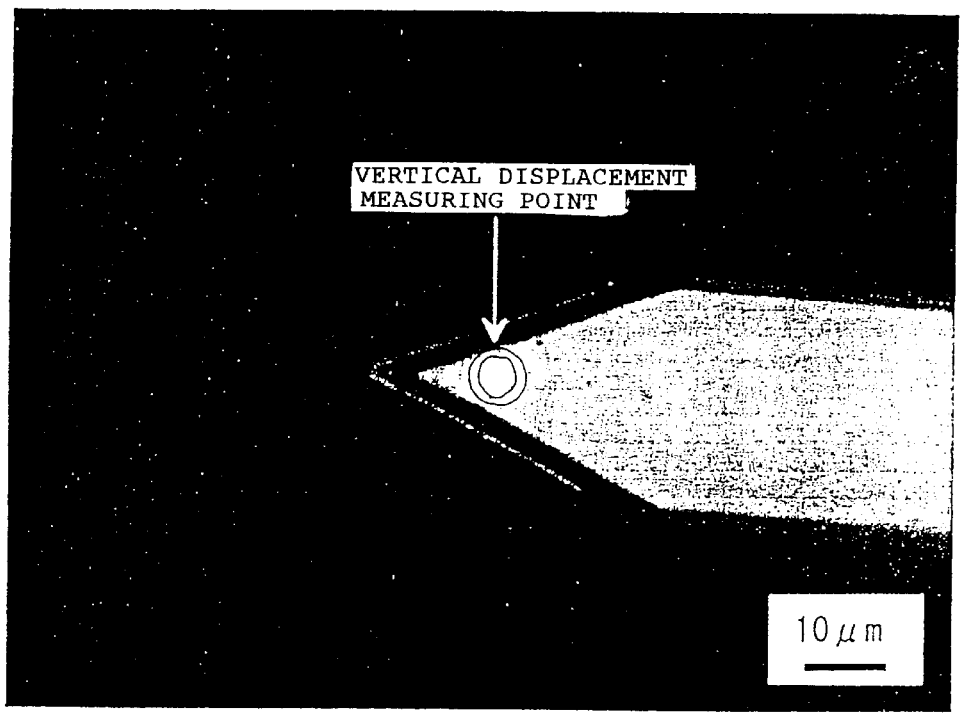
FIG. 10 is a photograph illustrating positioning by a silicon probe in a preferred embodiment according to the present invention.

FIG. 10 is a photograph illustrating that the positioning of the silicon probe is shot by the optical picture device (the CCD camera). At this time, the triaxial wide-area servo motor serving as the lever stand moving mechanism is controlled in such a manner that the tip of the silicon probe corresponds to the vertical displacement measuring point (indicated by a double circle in FIG. 10).

Figure 11:
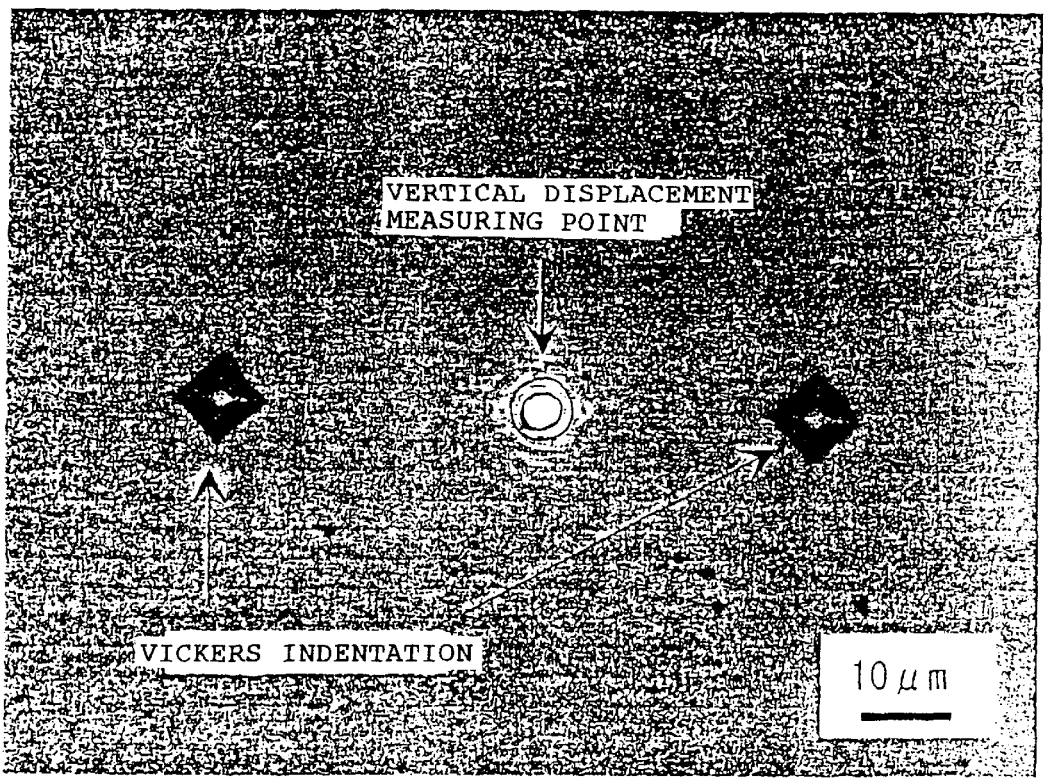
FIG. 11 is a photograph illustrating positioning by a diamond indenter in the preferred embodiment according to the present invention.

Similarly, FIG. 11 is a photograph illustrating that the positioning of the diamond indenter is shot by the CCD camera. Since the upper surface of the center lever provided with the diamond indenter is shot by the CCD camera when positioned by the diamond indenter, the position of the diamond indenter has been previously marked at the upper surface of the center lever. In this embodiment, two Vickers indentations have been marked, and the diamond indenter is then set at the middle point on a line connecting the two Vickers indentations.

The indentation hardness measuring test and the atomic force microscopic measurement were made on the tungsten single crystal electrolytic polishing surface.

Figure 12:
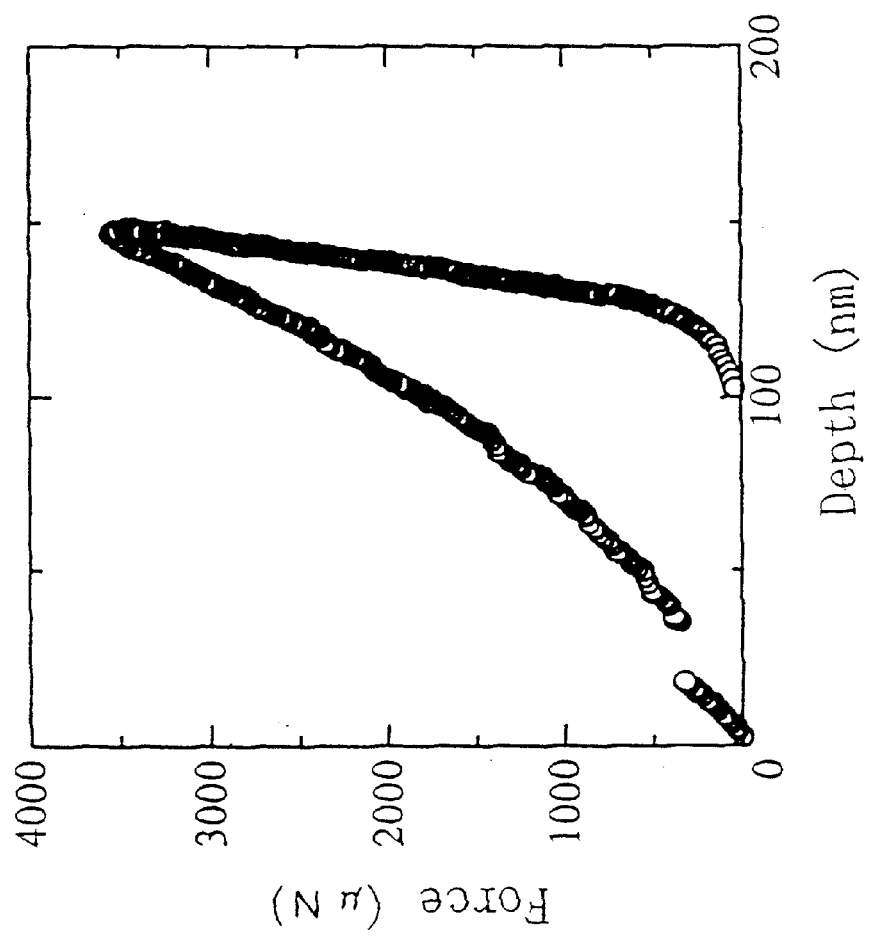
FIG. 12 is a graph illustrating a curve expressing the relationship between a force and a penetration depth of a tungsten single crystal electrolytic polishing surface measured in the preferred embodiment according to the present invention.

FIG. 12 is a graph illustrating a curve expressing the relationship between a force and a penetration depth of the tungsten single crystal electrolytic polishing surface, measured in the hardness measuring function mode by the ultra micro indentation testing apparatus according to the present invention.

Figure 13:
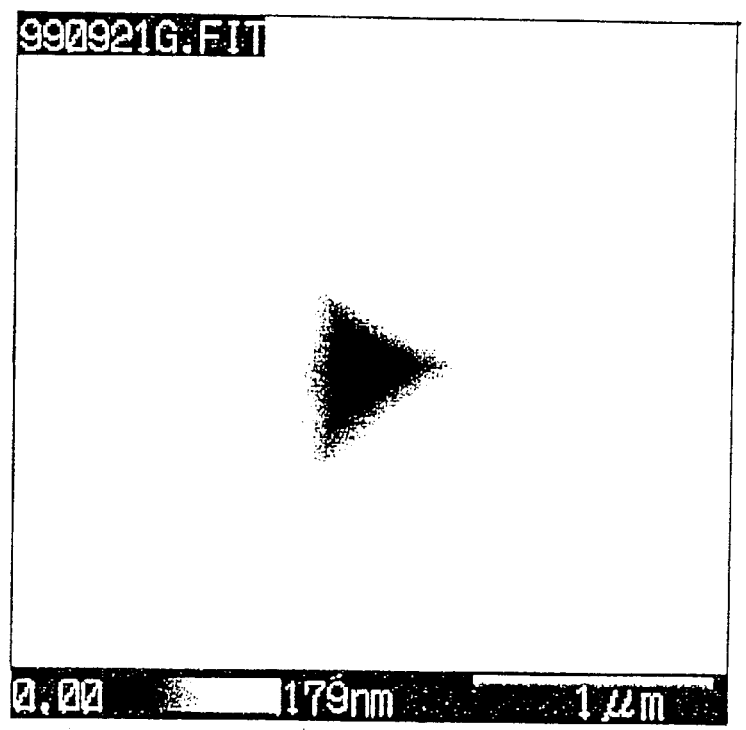
FIG. 13 illustrates an atomic force microscopic image of an indentation on the tungsten single crystal electrolytic polishing surface acquired by the use of the silicon probe in the preferred embodiment according to the present invention.
Figure 14:
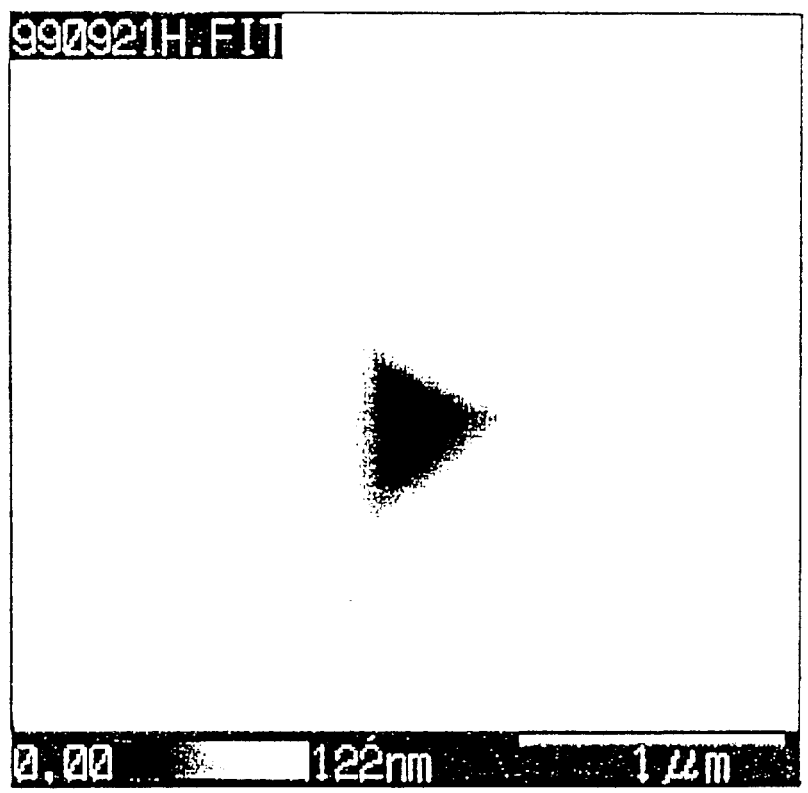
FIG. 14 illustrates an atomic force microscopic image of an indentation on the tungsten single crystal electrolytic polishing surface acquired by the use of the diamond indenter in the preferred embodiment according to the present invention.

After the indentation test, an image of the tungsten single crystal electrolytic polishing surface was acquired by the atomic force microscope by using the silicon probe and the diamond indenter in the atomic force microscopic function mode. FIG. 13 illustrates an atomic force microscopic image of the indentation acquired by the use of the silicon probe, and FIG. 14 illustrates an atomic force microscopic image of the indentation acquired by using the diamond indenter. A comparison of FIGS. 13 and 14 reveals that the edge of the indentation of the atomic force microscopic image by the silicon probe is more clearly obtained than that obtained by the diamond indenter. Further, the atomic force microscopic image by the silicon probe has a horizontal resolution higher than that obtained by the diamond indenter.

Figure 15:
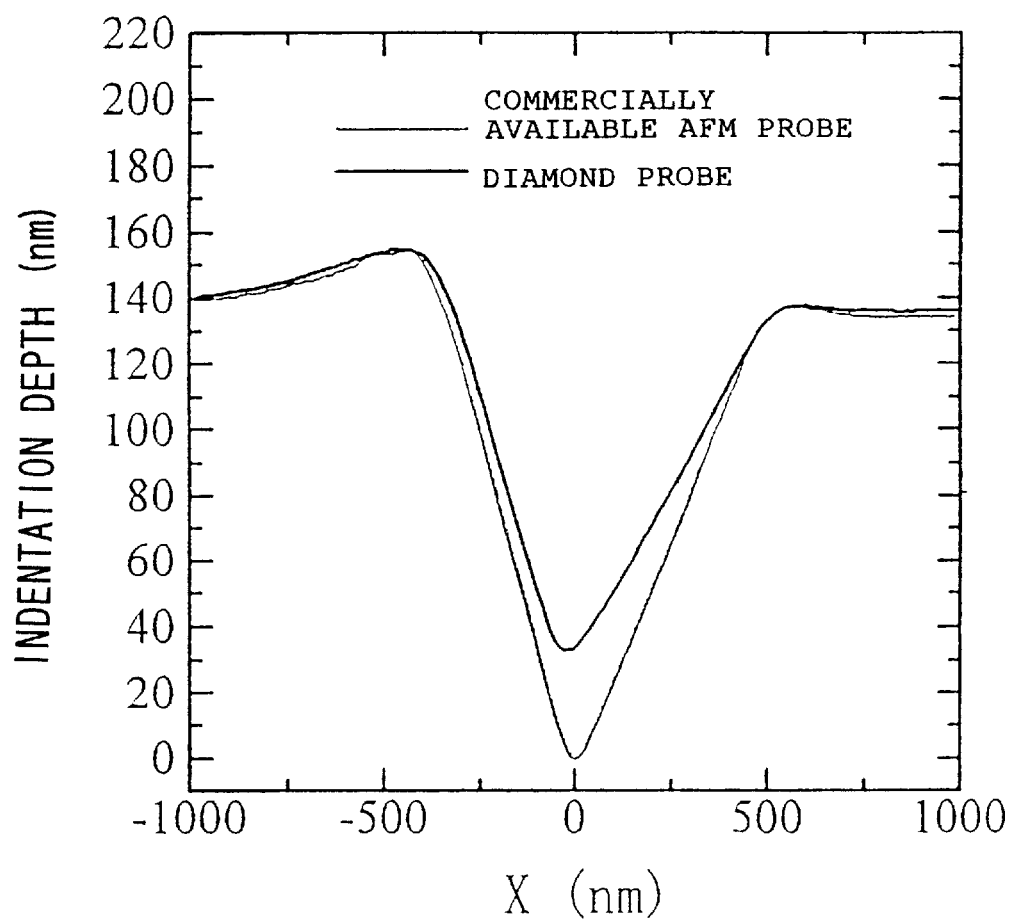
FIG. 15 illustrates the comparison result of cross sections of indentations at the tungsten single crystal electrolytic polishing surfaces measured by the silicon probe and the diamond indenter in the preferred embodiment according to the present invention.

Furthermore, FIG. 15 is a graph illustrating the comparison result of cross sections of the indentations by the silicon probe and the diamond indenter in the atomic force microscope mode, illustrated in FIGS. 13 and 14. It is found that the deepest portion of the indentation can be observed by the silicon probe better than the diamond indenter. From this result, it is found that the accuracy in the depth direction also is higher using the silicon probe. It can be construed that the shape of the tip of the silicon probe is sharper than that of the diamond indenter.

Additionally, the indentation hardness measuring test and the atomic force microscopic measurement were made on an SCM 440 steel electrolytic polishing surface.

Figure 16:
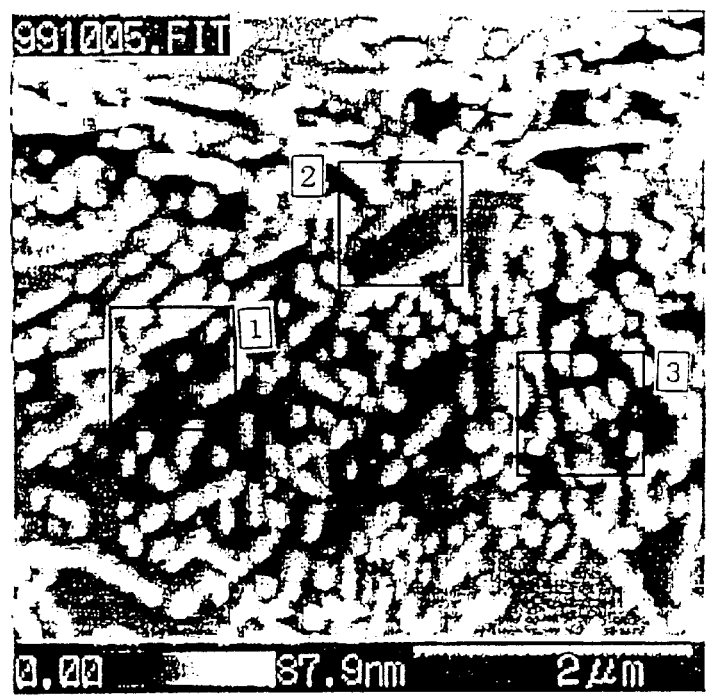
FIG. 16 illustrates an atomic force microscopic image of an SCM 440 steel electrolytic polishing surface acquired by the use of the silicon probe before an indentation hardness measuring test in the preferred embodiment according to the present invention.
Figure 17:
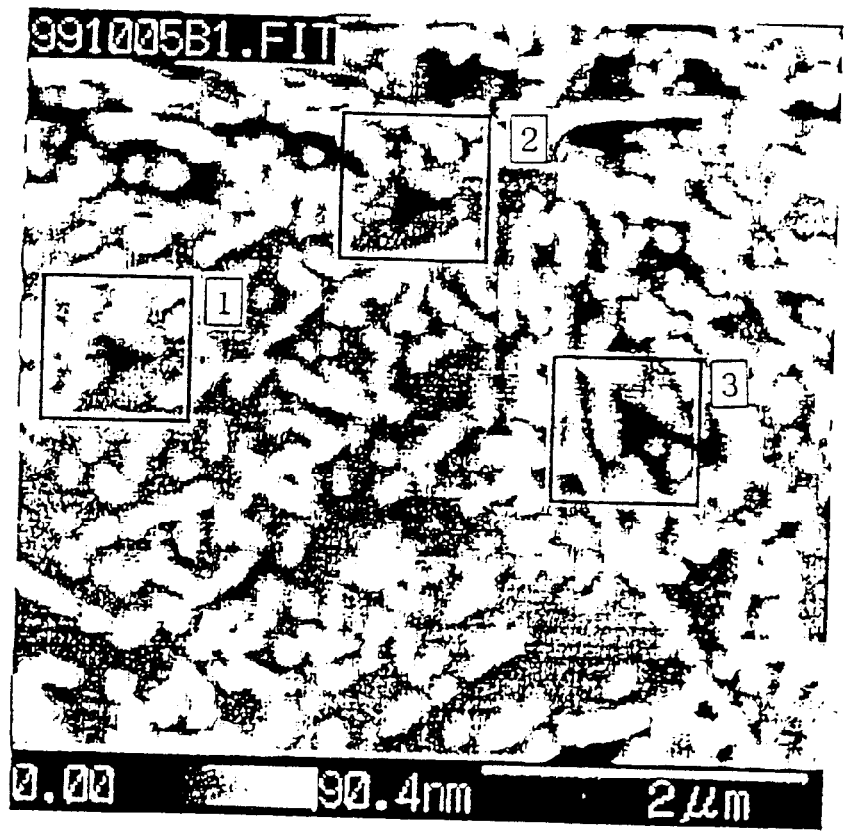
FIG. 17 illustrates an atomic force microscopic image of an SCM 440 steel electrolytic polishing surface acquired by the use of the silicon probe after the indentation hardness measuring test in the preferred embodiment according to the present invention.
Figure 18:
FIG. 18 is an enlarged view of the atomic force microscopic image of an indentation at the SCM 440 steel electrolytic polishing surface illustrated in FIG. 17.
Figure 18:
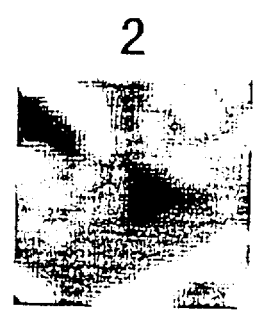
Figure 18:
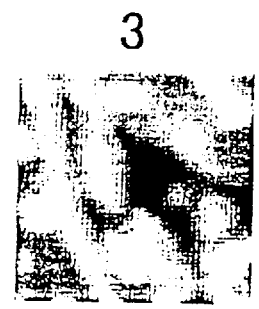
Figure 19:
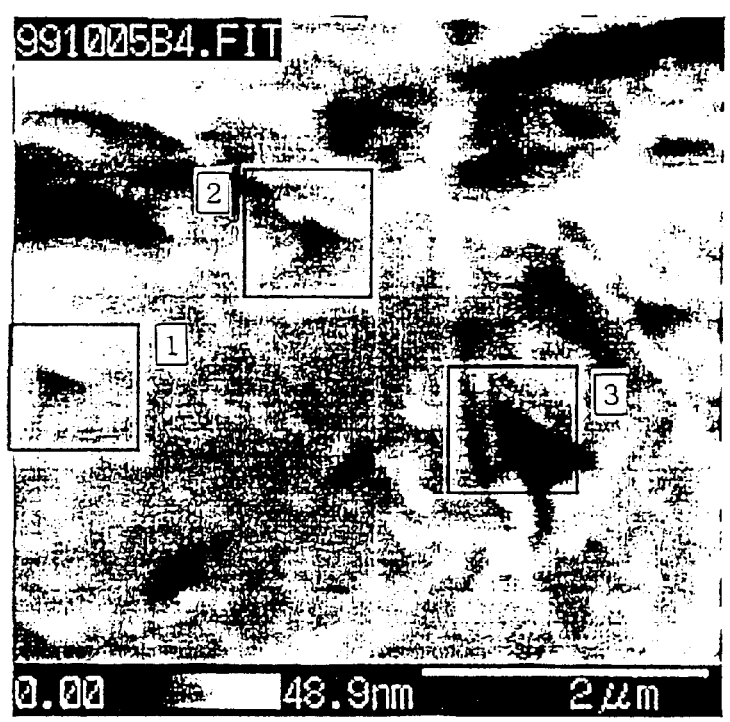
FIG. 19 illustrates an atomic force microscopic image of an SCM 440 steel electrolytic polishing surface acquired by the use of the diamond indenter after the indentation hardness measuring test in the preferred embodiment according to the present invention.
Figure 20:
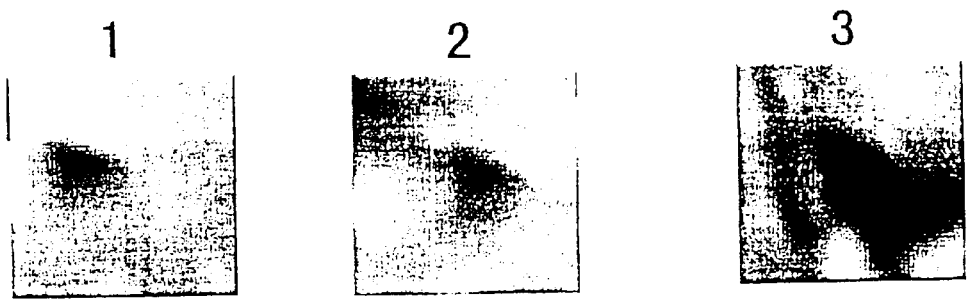
FIG. 20 is an enlarged view of the atomic force microscopic image of an indentation at the SCM 440 steel electrolytic polishing surface illustrated in FIG. 19.

FIG. 16 illustrates an atomic force microscopic image of the surface of the sample acquired by using the silicon probe before the indentation hardness measuring test. Here, the sample is an electrolytic polishing surface of SCM 440 steel (composed of 0.38% to 0.43% of C, 0.15% to 0.35% of Si, 0.60% to 0.85% of Mn, 0.030% or less of P, 0.030% or less of S, 0.90% to 1.20% of Cr and 0.15% to 0.30% of Mo) based on the JIS standard. The indentation hardness measuring test was performed in three regions 1 to 3 at the surface of the sample in FIG. 16 by the diamond indenter. FIG. 17 illustrates an atomic force microscopic image of an indentation acquired by using the silicon probe, and FIG. 18 is an enlarged view of the atomic force microscopic image of the indentation acquired by using the silicon probe. Moreover, FIG. 19 illustrates an atomic force microscopic image of an indentation acquired by using the diamond indenter, and FIG. 20 is an enlarged view of the atomic force microscopic image of the indentation acquired by using the diamond indenter. Also, from FIGS. 17 to 20, it is found that the resolution of the image acquired by the silicon probe is higher than that acquired by the diamond indenter, as described above.

Figure 21:
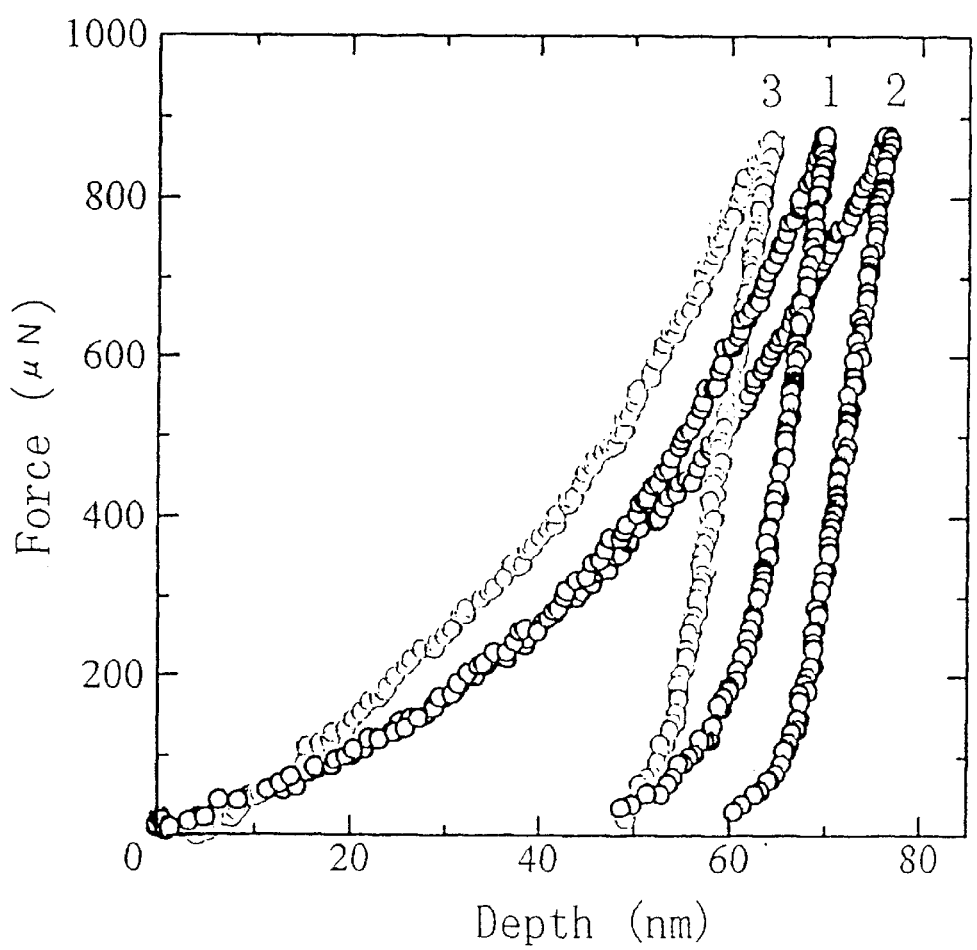
FIG. 21 is a graph illustrating a curve expressing the relationship between a force and a penetration depth of the SCM 440 steel electrolytic polishing surface measured in the preferred embodiment according to the present invention.
Figure 22:
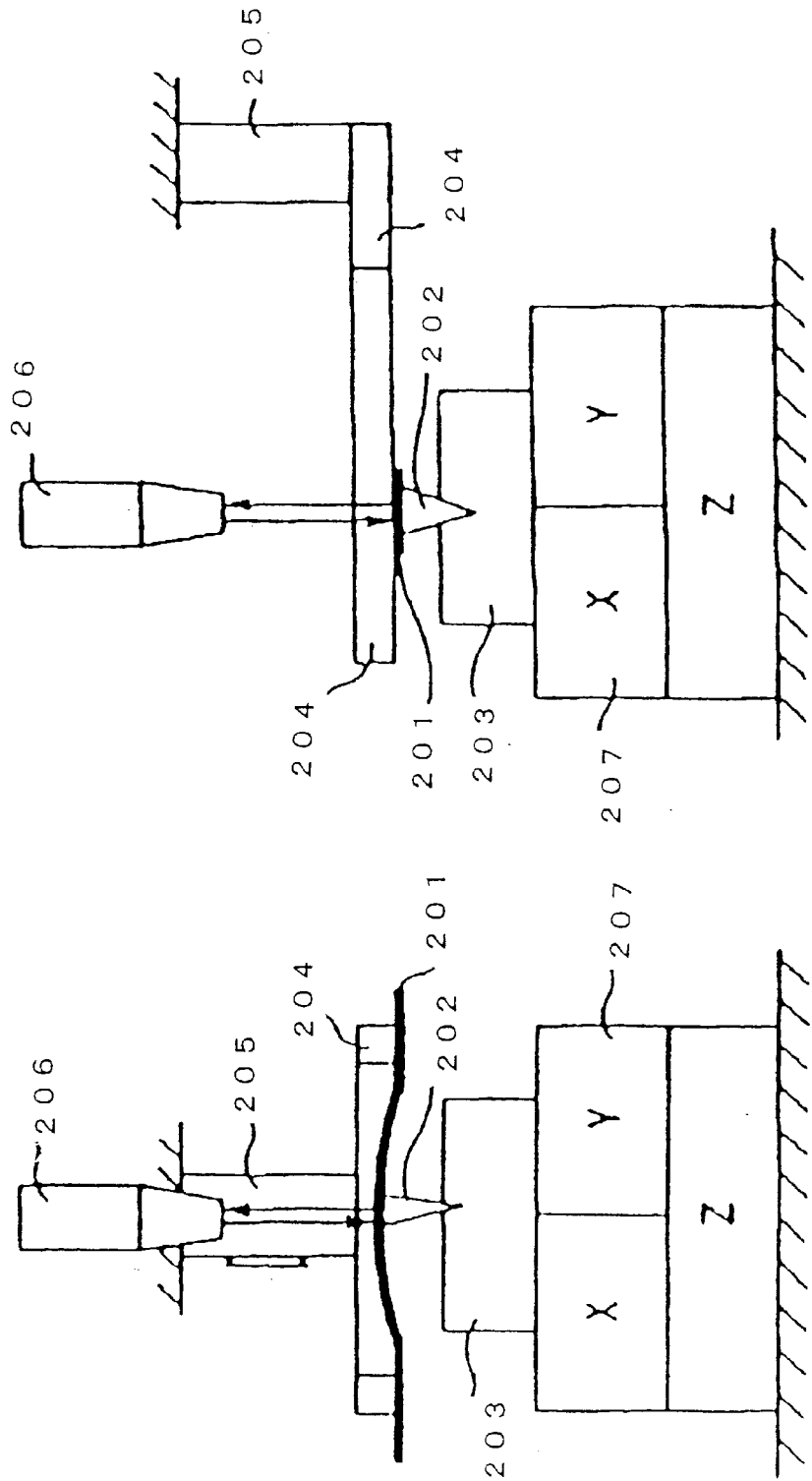
FIG. 22 is a view schematically showing the configuration of a surface hardness measuring apparatus in the prior art.
Figure 23:
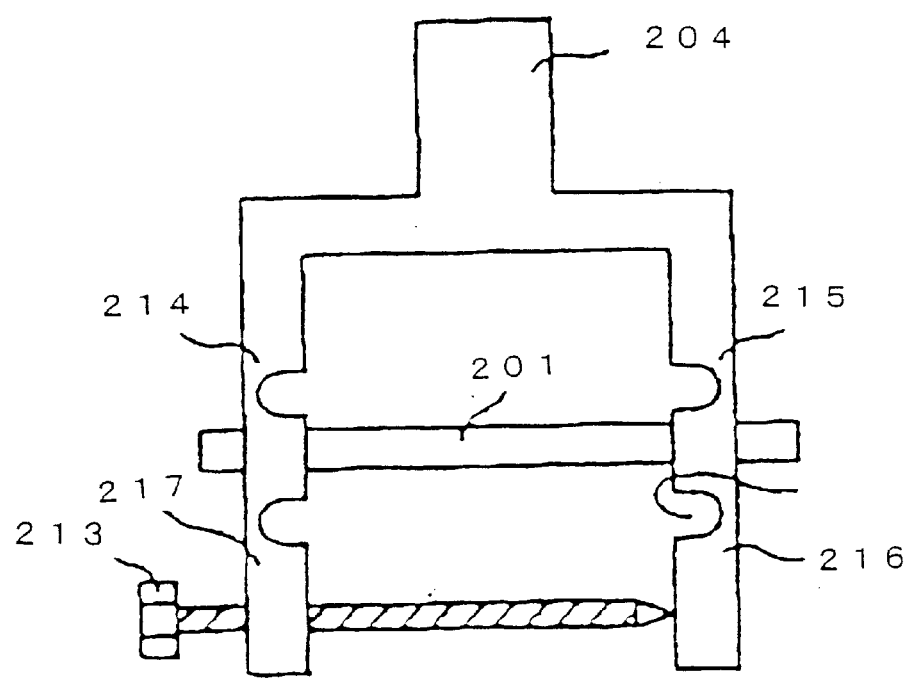
FIG. 23 is a view schematically showing the configuration of a lever and a lever stand in the surface hardness measuring apparatus in the prior art.
Figure 23:
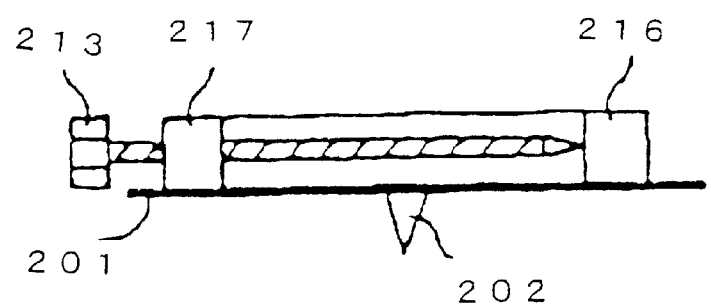

The silicon probe enables the distribution of fine carbide to be clearly identified. FIGS. 16 to 18 reveal that a small quantity of carbide is present in a region 2, and no carbide is present at a pushed-in portion. Similarly, it is revealed that a largest quantity of carbide is present in a region 3, and the pushed-in portion is located just above carbide. The result of the indentation hardness measuring test illustrated in FIG. 21 shows that the hardness in the region 2 is lowest while the hardness in the region 3 is highest. Therefore, it is determined that the hardness depends upon the presence of carbide.

Thus, the atomic force microscopic image of a high resolution is very useful in interpreting the curve expressing the relationship between the force and the penetration depth, and is very important for the research and development of the mechanical characteristics of the material in the minute region.

INDUSTRIAL APPLICABILITY

As described above in detail, according to the present invention, an ultra micro indentation testing apparatus useful for the research and development of the functional material in the minute region is provided. In particular, it is expected that the mechanical properties of the fine structure of a semiconductor or an advanced functional material such as super steel will be elucidated to remarkably promote the development of such material.

Furthermore, the indirect effect produced by the present invention is very profound in considering that only as small an installation space as that required by the conventional indentation hardness testing apparatus is required in spite of the testing apparatus having, in combination, an optical microscopic function, an atomic force microscopic function, and a hardness measuring function, and that the testing apparatus having the functions in combination can be fabricated at a more reduced cost than that of independently fabricating apparatuses having respective functions.

What is claimed is:

1. An ultra micro indentation testing apparatus comprising:
    a lever holder including a center lever, a probe, and an indenter;
    a moving mechanism for moving said lever holder in a triaxial direction;
    an indentation mechanism for pushing said indenter into a sample;
    a displacement gage for measuring a displacement of one of said probe and said indenter; and
    an optical picture device for assisting in positioning one of said probe and said indenter, and for observing a surface of the sample;
    wherein said lever holder, said moving mechanism, said indentation mechanism, said displacement gage, and said optical picture device are arranged and operable to perform:
        a hardness measuring function based on a measurement of a force and a depth of said indenter pushed in the surface of the sample;
        an atomic force microscopic function of acquiring a shape of the surface of the sample based on a displacement of said one of said probe and said indenter; and
        an optical microscopic function of observing the surface of the sample using said optical picture device.

2. The ultra micro indentation testing apparatus of claim 1, wherein said center lever is arranged in a hole in a center of said lever holder.

3. The ultra micro indentation testing apparatus of claim 2, wherein a side face of said lever holder has grooves for holding said center lever in a desired position.

4. The ultra micro indentation testing apparatus of claim 2, wherein said indenter is arranged on said center lever, and said center lever has a positioning mark formed thereon.

5. The ultra micro indentation testing apparatus of claim 2, wherein said lever holder includes a plurality of probes.

6. The ultra micro indentation testing apparatus of claim 2, wherein said lever holder includes a plurality of center levers.

7. The ultra micro indentation testing apparatus of claim 2, wherein said probe is made of silicon, and said indenter is made of diamond.

8. The ultra micro indentation testing apparatus of claim 2, further comprising a remote control mechanism for remotely controlling a movement of said lever holder with an accuracy on the order of a micrometer.

9. The ultra micro indentation testing apparatus of claim 1, wherein a side face of said lever holder has grooves for holding said center lever in a desired position.

10. The ultra micro indentation testing apparatus of claim 9, wherein said indenter is arranged on said center lever, and said center lever has a positioning mark formed thereon.

11. The ultra micro indentation testing apparatus of claim 9, wherein said lever holder includes a plurality of probes.

12. The ultra micro indentation testing apparatus of claim 9, wherein said lever holder includes a plurality of center levers.

13. The ultra micro indentation testing apparatus of claim 9, wherein said probe is made of silicon, and said indenter is made of diamond.

14. The ultra micro indentation testing apparatus of claim 9, further comprising a remote control mechanism for remotely controlling a movement of said lever holder with an accuracy on the order of a micrometer.

15. The ultra micro indentation testing apparatus of claim 1, wherein said indenter is arranged on said center lever, and said center lever has a positioning mark formed thereon.

16. The ultra micro indentation testing apparatus of claim 15, wherein said lever holder includes a plurality of probes.

17. The ultra micro indentation testing apparatus of claim 15, wherein said lever holder includes a plurality of center levers.

18. The ultra micro indentation testing apparatus of claim 15, wherein said probe is made of silicon, and said indenter is made of diamond.

19. The ultra micro indentation testing apparatus of claim 15, further comprising a remote control mechanism for remotely controlling a movement of said lever holder with an accuracy on the order of a micrometer.

20. The ultra micro indentation testing apparatus of claim 1, wherein said lever holder includes a plurality of probes.

21. The ultra micro indentation testing apparatus of claim 20, wherein said lever holder includes a plurality of center levers.

22. The ultra micro indentation testing apparatus of claim 20, wherein said probe is made of silicon, and said indenter is made of diamond.

23. The ultra micro indentation testing apparatus of claim 20, further comprising a remote control mechanism for remotely controlling a movement of said lever holder with an accuracy on the order of a micrometer.

24. The ultra micro indentation testing apparatus of claim 1, wherein said lever holder includes a plurality of center levers.

25. The ultra micro indentation testing apparatus of claim 24, wherein said probe is made of silicon, and said indenter is made of diamond.

26. The ultra micro indentation testing apparatus of claim 24, further comprising a remote control mechanism for remotely controlling a movement of said lever holder with an accuracy on the order of a micrometer.

27. The ultra micro indentation testing apparatus of claim 1, wherein said probe is made of silicon, and said indenter is made of diamond.

28. The ultra micro indentation testing apparatus of claim 27, further comprising a remote control mechanism for remotely controlling a movement of said lever holder with an accuracy on the order of a micrometer.

29. The ultra micro indentation testing apparatus of claim 1, further comprising a remote control mechanism for remotely controlling a movement of said lever holder with an accuracy on the order of a micrometer.

* * * * *

UNITED STATES PATENT AND TRADEMARK OFFICE
CERTIFICATE OF CORRECTION

PATENT NO. : 6,755,075 B2
DATED : June 29, 2004
INVENTOR(S) : Nobuo Nagashima et al.

It is certified that error appears in the above-identified patent and that said Letters Patent is hereby corrected as shown below:

<u>Title page,</u>
Item [73], Assignee, please change from "Japanese Science and Technology Corporation" to -- Japan Science and Technology Corporation --.

Signed and Sealed this

Thirtieth Day of November, 2004

JON W. DUDAS
*Director of the United States Patent and Trademark Office*